United States Patent [19]

Saville

[11] Plant 5,141

[45] Nov. 22, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 342,658

[22] Filed: Jan. 25, 1982

[51] Int. Cl.[3] ..... A01H 5/00

[52] U.S. Cl. ..... Plt./8

[58] Field of Search ..... Plt./7, 8

*Primary Examiner*—Robert E. Bagwill

*Attorney, Agent, or Firm*—Vincent G. Gioia

[57] ABSTRACT

A new miniature rose variety of bright yellow coloring borne singly and in large sprays.

1 Drawing Figure

The present invention relates to a new and distinct variety of rose plant of the miniature rose class, which was originated by my crossing as seed parent the rose known as "Rise N' Shine" and the deep yellow rose known as "Kiskadee" as pollen parent. The generic name of this variety is "Savacent" and the commercial appellation is "Center Gold".

Among the novel characteristics possessed by this new variety which distinguish it from its parents and all other varieties of which I am aware are high centered, heavily petaled flowers of bright yellow coloring. Flowers, which are borne singly and in large sprays, are attractively contrasted against attractive green foliage which is textured like the rose "Arthur Bell". Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "15B" is plate 15B of the Royal Horticultural Society Colour Chart.

Parentage: Seedling.
*Seed parent.*—"Rise N' Shine".
*Pollen parent.*—"Kiskadee".
Class: Miniature.

The following observations are made of specimens grown outdoors in Essex County, Mass. during the month of October.

1. FLOWER

Blooming habit: Fast recurrent.

A. Bud:
(1) *Size.*—Medium.
(2) *Form.*—Pointed, ovate.
(3) *Color.*—When sepals first divide — 15B.
(4) *Sepals.*—Normal slightly foliated.

(5) *Peduncle.*—Length — about 1 inch. Aspect — Straight. Strength — Erect. Color — 144D.

B. Bloom:
(1) *Size.*—Average size when fully expanded — about 1½ inches.
(2) *Borne.*—Singly and in sprays of 3 to 12 blooms.
(3) *Form.*—High centered at first reflexing as bloom matures.
(4) *Petalage.*—Number of petals under normal conditions — about 55 to 65.
(5) *Color.*—Yellow buds open into attractive high centered bright yellow, near 15B, flowers with inner petals indicating some blending with 22C in the very deep center. Outer petals are near 15B lightening to 15D toward petal edges with 11D at point of petal attachment. The general tonality from a distance is golden yellow when flowers are half open. As blooms age flower color lightens considerably. As blossoms open fully, color pales considerably. Outer petals quill and turn pure white and as blossom ages further, the entire blossom becomes pure white. All petals are held and recurl to ball-like form of pure white with no discoloration. An unusual characteristic of this variety is that the plant occasionally develops a near white bloom sometimes even on the same cane with other normal yellow colored flowers. This characteristic is somewhat more prevalent with an increase in fertilization level.

C. Petals:
(1) *Texture.*—Thick.
(2) *Appearance.*—Velvety with veining.
(3) *Form.*—Fan shaped quilling to points.
(4) *Arrangement.*—Regularly arranged, shingle-like.
(5) *Petaloids in center.*—Normal.
(6) *Persistence.*—Drop off cleanly.
(7) *Fragrance.*—Sweet, spicy.
(8) *Lasting quality.*—Long lasting on plant and when cut.

2. REPRODUCTIVE ORGANS

A. Stamens, filaments and anthers:
(1) *Arrangement.*—Irregular, sparse.
(2) *Color.*—Light yellow.

B. Pollen:
*Color.*—Light yellow.

C. Styles: Bunched, uneven length.

D. Stigmas:

*Color.*—Light yellow green.

E. Hips:

*Shape.*—Globular.

*Size.*—About ¾ inch diameter.

*Color.*—Orange, about 33A.

*Do seeds protrude?*—No.

3. PLANT

A. Form: Upright, compact.

B. Growth: Very vigorous.

*Height attained.*—About 15 to 18 inches.

C. Foliage: Compound 5 to 7 leaflets.

(1) *Size.*—Medium.

(2) *Quantity.*—Abundant, profuse.

(3) *Color.*—Foliage: Dark green.

(4) *Shape.*—Oval.

(5) *Texture.*—Glossy and textured like the rose "Arthur Bell" and under side is matte.

(6) *Edge.*—Serrate.

(7) *Serration.*—Medium.

(8) *Leaf stem.*—Color — green.

(9) *Stipules.*—Medium.

(10) *Resistance to disease.*—Blackspot — Average. Mildew — Average. Rust — Average.

D. Wood:

(1) *New wood.*—Color — Near 144A. Bark — Smooth.

(2) *Old wood.*—Color — Near 191A. Bark — Rough.

E. Thorns:

(1) *Thorns.*—Quantity (main stalk): Average. On laterals from stalk — Average. Form — Long thin pointed angled slightly downward. Length — Medium. Color — Near 145C. Position — Irregular.

(2) *Prickles.*—None.

F. Winter hardiness: Average.

I claim:

1. A new and distinct variety of rose plant of the miniature class, substantially as shown and described, characterized particularly by high centered, bright yellow blooms of heavy petallage borne singly and in large sprays (3 to 12 blooms).

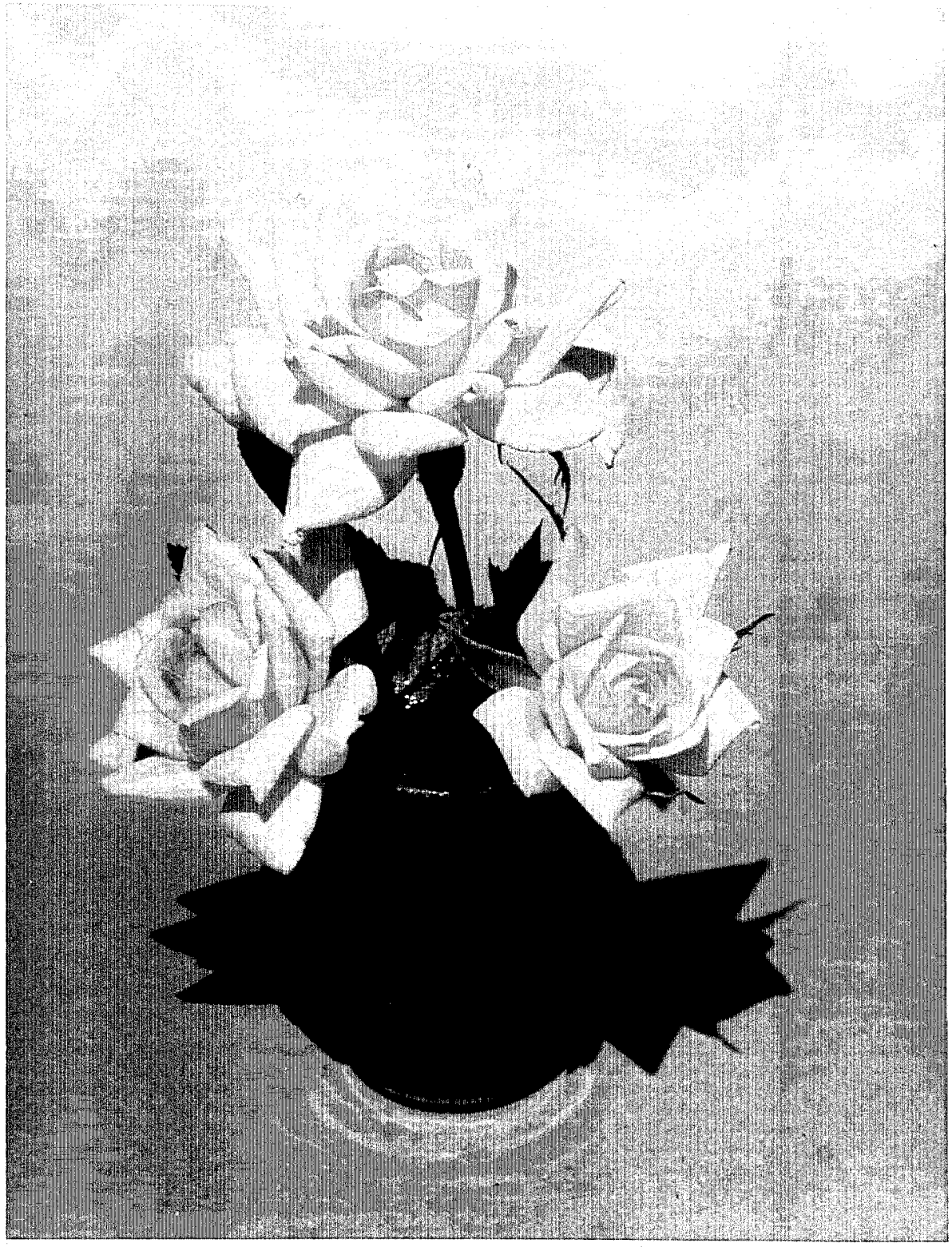

* * * * *